United States Patent [19]

Barrish et al.

[11] Patent Number: 4,946,840
[45] Date of Patent: Aug. 7, 1990

[54] BENZAZEPINE AND BENZOTHIAZEPINE DERIVATIVES

[75] Inventors: Joel C. Barrish, Holland, Pa.; Spencer D. Kimball, East Windsor; John Krapcho, Somerset, both of N.J.

[73] Assignee: E. R. Squibb & Sons, Inc., Princeton, N.J.

[21] Appl. No.: 334,025

[22] Filed: Apr. 6, 1989

[51] Int. Cl.$^5$ .................... A61K 31/55; C07D 417/12; C07D 405/12
[52] U.S. Cl. .................................. 514/211; 514/213; 540/491; 540/523
[58] Field of Search .............. 540/491, 523; 514/211, 514/213

[56] References Cited

U.S. PATENT DOCUMENTS

| | | | |
|---|---|---|---|
| 3,562,257 | 2/1971 | Kugita et al. | 540/491 |
| 4,567,175 | 1/1986 | Takeda et al. | 540/491 |
| 4,584,131 | 4/1986 | Floyd et al. | 540/491 |
| 4,590,188 | 5/1986 | Takeda et al. | 540/491 |
| 4,694,002 | 9/1987 | Floyd et al. | 540/491 |
| 4,748,239 | 5/1988 | Floyd et al. | 540/491 |
| 4,752,645 | 6/1988 | Das et al. | 540/491 |

FOREIGN PATENT DOCUMENTS

| | | | |
|---|---|---|---|
| 292840 | 5/1987 | European Pat. Off. | 540/523 |
| 0256888 | 2/1988 | European Pat. Off. | 540/491 |
| 0289241 | 11/1988 | European Pat. Off. | 540/491 |

OTHER PUBLICATIONS

L. H. Werner et al., "Imidazoline Derivatives with Antiarrhythmic Activity" *J. Med. Chem.*, 1967, 10, 575–582.

*Primary Examiner*—Robert T. Bond
*Attorney, Agent, or Firm*—Timothy J. Gaul

[57] ABSTRACT

Vasodilating activity is exhibited by compounds having the formula

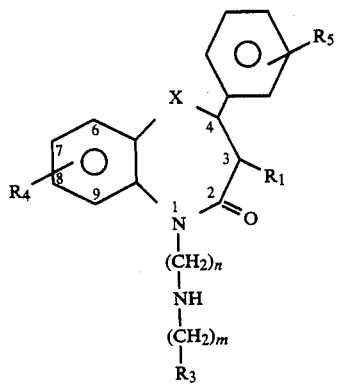

and the pharmaceutically acceptable salts thereof, wherein
X is —CH$_2$— or —S—;
R$_1$ is

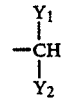

or —O—Y$_3$;
R$_2$ is heterocyclo or heteroaryl;
R$_3$ and R$_4$ are each independently hydrogen, halogen, alkyl, alkoxy, aryloxy, arylalkoxy, arylalkyl, cyano, hydroxy, alkanoyloxy,

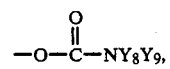

fluoro-substituted alkoxy, fluoro-substituted alkyl, (cycloalkyl)alkyl, —NO$_2$, —NY$_{10}$Y$_{11}$, —S(O)$_k$alkyl, —S(O)$_k$aryl

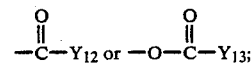

n is 0, 1, 2 or 3;
m is 0, 1, 2 or 3;
k is 0, 1 or 2;
Y$_1$ and Y$_2$ are each independently hydrogen or alkyl; or Y$_1$ is hydrogen and Y$_2$ is alkenyl, alkynyl, aryl, heteroaryl, or cycloalkyl; or Y$_1$ and Y$_2$, together with the carbon atom to which they are attached, are cycloalkyl;
Y$_3$ is hydrogen, alkyl, alkanoyl, alkenyl, arylcarbonyl, heteroarylcarbonyl, or

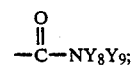

Y$_8$ and Y$_9$ are each independently hydrogen, alkyl, aryl, or heteroaryl; or Y$_8$ and Y$_9$, together with the nitrogen atom to which they are attached, are pyrrolidinyl, piperidinyl or morpholinyl;
Y$_{10}$ and Y$_{11}$ are each independently hydrogen, alkyl, alkanoyl, arylcarbonyl, heteroarylcarbonyl, or

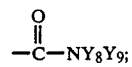

Y$_{12}$ is hydroxy, alkoxy, aryloxy, amino, alkylamino, or dialkylamino; and
Y$_{13}$ is alkyl, alkoxy or aryloxy.

18 Claims, No Drawings

BENZAZEPINE AND BENZOTHIAZEPINE DERIVATIVES

BRIEF DESCRIPTION OF THE INVENTION

Compounds having the formula

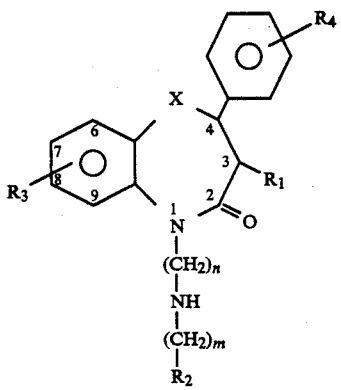

and the pharmaceutically acceptable salts thereof possess calcium entry blockade activity and so are useful, for example, as cardiovascular agents. In formula I, and throughout the specification, the symbols are as defined below.

X is —$CH_2$— or —S—;

$R_1$ is

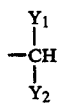

or —O—$Y_3$;

$R_2$ is heterocyclo or heteroaryl;

$R_3$ and $R_4$ are each independently hydrogen, halogen, alkyl, alkoxy, aryloxy, arylalkoxy, arylalkyl, cyano, hydroxy, alkanoyloxy,

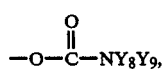

fluoro-substituted alkoxy, fluoro-substituted alkyl, (cycloalkyl)alkoxy, —$NO_2$, —$NY_{10}Y_{11}$, —$S(O)_k$alkyl, —$S(O)_k$aryl

or —O—C—$Y_{13}$;

n is 2 or 3;
m is 0, 1, 2 or 3;
k is 0, 1 or 2;

$Y_1$ and $Y_2$ are each independently hydrogen or alkyl; or $Y_1$ is hydrogen and $Y_2$ is alkenyl, alkynyl, aryl, heteroaryl, or cycloalkyl; or $Y_1$ and $Y_2$, together with the carbon atom to which they are attached, are cycloalkyl;

$Y_3$ is hydrogen, alkyl, alkanoyl, alkenyl, arylcarbonyl, heteroarylcarbonyl, or

$Y_8$ and $Y_9$ are each independently hydrogen, alkyl, aryl, or heteroaryl; or $Y_8$ and $Y_9$, together with the nitrogen atom to which they are attached, are pyrrolidinyl, piperidinyl or morpholinyl;

$Y_{10}$ and $Y_{11}$ are each independently hydrogen, alkyl, alkanoyl, arylcarbonyl, heteroarylcarbonyl, or

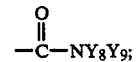

$Y_{12}$ is hydroxy, alkoxy, aryloxy, amino, alkylamino, or dialkylamino; and $Y_{13}$ is alkyl, alkoxy or aryloxy.

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are substituted with 1, 2 or 3 amino (—$NH_2$), alkylamino, dialkylamino, nitro, halogen, hydroxyl, trifluoromethyl, alkyl (of 1 to 4 carbon atoms), alkoxy (of 1 to 4 carbon atoms), alkylthio (of 1 to 4 carbon atoms), alkanoyloxy, carbamoyl, or carboxyl groups.

The term "alkanoyl" refers to groups having the formula alkyl

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furanyl, thienyl, or thiazolyl.

The term "heterocyclo" refers to fully saturated or unsaturated rings of 5 or 6 atoms containing one or two oxygen and sulfur atoms and/or one to four nitrogen atoms, provided that the total number of hetero atoms in the ring is 4 or less. The hetero ring is attached by way of an available carbon atom. The term "heterocyclo" also includes bicyclic rings wherein the five- or six-membered ring containing oxygen, sulfur, or nitrogen atoms as defined above is fused to a benzene ring and the bicyclic ring is attached by way of an available carbon atom in the benzene ring. The term "heterocyclo" further includes such monocyclic and bicyclic rings wherein an available carbon atom is substituted with:

a lower alkyl of 1 to 4 carbons;
a lower alkylthio of 1 to 4 carbons;
a lower alkoxy of 1 to 4 carbons;

a halo;
a nitro;
a keto;
a cyano;
a hydroxy;
an amino;
—NH—alkyl, wherein the alkyl is of 1 to 4 carbons;
—N(alkyl)$_2$, wherein the alkyl is of 1 to 4 carbons;
—CF$_3$;
—NCS; or
OCHF$_2$.

The term "heterocyclo" further includes monocyclic and bicyclic rings wherein two or three available carbons have substituents selected from methyl, methoxy, methylthio, halo, CF$_3$, nitro, hydroxy, amino, and OCHF$_2$.

The term "cycloalkyl" refer to groups having 3, 4, 5, 6 or 7 carbon atoms.

The terms "halogen" and "halo" refer to fluorine, chlorine, bromine and iodine.

The terms "fluoro-substituted alkyl" and "fluoro-substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization with, for example, a base such as sodium hydroxide. Any other salt may then be formed from the free base and the appropriate inorganic or organic acid. Illustrative are the hydrohalides (especially hydrochloride and hydrobromide), fumarate, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3- and 4-positions of the benzazepine nucleus of formula I compounds are asymmetric carbons. The carbon atoms in the 2-and 3-position of the benzothiazepine nucleus of formula I are also asymmetric carbons. The compounds of formula I, therefore, exist in enantiomeric and diastereomeric forms and as racemic mixtures thereof. All are within the scope of this invention. It is believed that formula I compounds having the d-cis configuration are the most potent and are therefore preferred.

Also preferred are compounds in which:
R$_1$ is hydroxyl;
R$_2$ is imidazolyl, furanyl, pyridinyl, methylpyrrolyl, methylindolyl, piperidinyl, or morpholinyl;
R$_3$ is trifluoromethyl; and
R$_4$ is methoxy.

The R$_2$ groups vary in their point of bonding to the —(CH$_2$)$_m$— portion of compounds having formula I. Although all compounds of formula I are believed to have useful activity, R$_2$ groups are preferred to be bonded as follows:
imidazolyl at the 1-position;
pyridinyl at the 4- or 2-position;
methylpyrrolyl at the 2-position;
methylindolyl at the 1-position;
furanyl at the 2-position;
piperidinyl at the 1-position; and
morpholinyl at the 4-position.

DETAILED DESCRIPTION OF THE INVENTION

The compounds of formula I and the pharmaceutically acceptable salts thereof are useful as cardiovascular agents. These compounds act as vasodilators and are especially useful as anti-hypertensive agents. Because of their vasodilating activity, formula I compounds may also be useful in limiting myocardial infarction and as anti-arrhythmic, anti-anginal, anti-fibrillatory, anti-asthmatic, and anti-ischemic agents.

Administration of a composition containing one or a combination of these compounds reduces the blood pressure of a hypertensive mammalian host (e.g., human). Single or divided daily doses of about 0.1 to 20 mg per kilogram of body weight per day (preferably about 0.5 to about 10 mg per kilogram per day) are appropriate to reduce blood pressure. Although oral administration is preferred, one can also use subcutaneous, intramuscular, intravenous, or other parenteral routes.

Formula I compounds can also be combined with a diuretic or an angiotensin-converting enzyme inhibitor. Suitable diuretics include hydrochlorothiazide and bendroflumethiazide, and other thiazide diuretics. Suitable angiotensinconverting enzyme inhibitors include captopril, zofenopril, fosinopril, enalapril, and lisinopril.

Formula I compounds can be prepared by the following exemplary process.

Formula I compounds can be derived from compounds having the formula or salts thereof, such as Racemic and nonracemic forms of formula II and IIa compounds are readily obtainable using methodology disclosed in U.S. Pat. Nos. 4,748,239; 4,752,645; and 3,562,257. For example, Examples 30 and 43 of the '239 patent describe preparation of formula II and IIa compounds wherein X is —CH$_2$—.

A formula II or IIa compound is treated with, in sequence:

(1) a base (e.g., sodium hydride) in an inert solvent (e.g., dimethylformamide), (2) an alkylating agent of the formula III Halo—(CH$_2$)$_n$—CH=CH$_2$, and (3) ozone in an organic solvent (e.g., methylene chloride), to form a compound of the formula

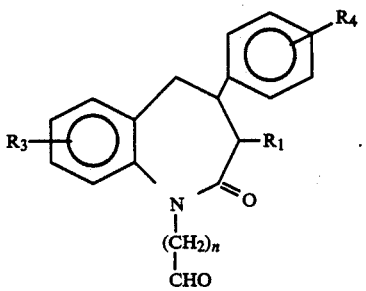
                                                                IV

When R$_1$ is —O—Y$_3$ and Y$_3$ is other than hydrogen, such formula IV compounds can be obtained by alkylation or acylation (using conventional techniques) of the corresponding compound in which R$_1$ is —OH.

A compound formula I is formed by hydrogenating a mixture of
(1) a compound of formula IV, and
(2) a compound of formula

                                                                V

An exemplary process places a formula IV compound, a formula V compound, and a catalyst (e.g., palladium on charcoal) in a methanol solvent. The formula IV compound thus reacts with the formula V compound to yield the free base of a corresponding formula I compound. The free base is then treated with an acid (such as oxalic acid, fumaric acid, or hydrogen chloride-saturated ether) to yield a compound of formula I.

Alternatively, compounds of formula I can be prepared by reacting a compound of formula II with a compound of formula Z—(CH$_2$)$_n$—NR$_5$—(CH$_2$)$_m$—R$_2$     (VI)

wherein Z is a leaving group such as halo, and R$_5$ is alkyl, aryl, arylalkyl, heterocyclo or heteroaryl (but not olefin). The reaction is effectuated by heating compound II and compound VI in a solvent such as acetone or butanone in the presence of a base such as potassium carbonate.

Another preparation of compounds of formula I involves reacting a compound of formula II with a compound of formula VI wherein R$_2$ is a protecting group such as t-butoxycarbonyl or benzyloxycarbonyl. This reaction is effectuated by heating compound II and compound VI in a solvent such as dimethylformamide in the presence of a base such as cesium carbonate. The resulting compound of formula I wherein R$_2$ is a protecting group is converted into a compound of formula I wherein R$_2$ is H by known art. This method is preferred for preparation of compounds of formula I.

The following are examples of specific embodiments of the invention.

EXAMPLE 1

(3R-cis)-1,3,4,5-Tetrahydro-3-hydroxy-4-(4-methoxyphenyl)-1-[2-[[2-(1-piperidinyl)ethyl]amino]ethyl]-6-(trifluoromethyl)-2H-1-benzazepin-2-one, dihydrochloride.

Step 1: Preparation of (3R-cis)-1,3,4,5-tetrahydro-1-allyl-3-hydroxy-4-(4-methoxyphenyl)-6-(trifluoromethyl)-2H-1-benzazepin-2-one 60% Sodium hydride (0.54 g; 13.5 mmol) was added to (3R-cis)-1,3,4,5-tetrahydro-3-hydroxy-4-(4-methoxyphenyl)-6-(trifluoromethyl)-2H-1benzazepin-2-one, (prepared as described in U.S. Pat. No. 4,748,239, Example 30, part F), (5.00 g, 14.2 mmol) in dry dimethylformamide (50 ml) under nitrogen, and the mixture was stirred at room temperature for 20 minutes. The anion mixture was cooled to 0° C. and allyl bromide (1.17 ml; 13.5 mmol) was added and the mixture was stirred overnight, allowing it to gradually reach room temperature. The reaction was quenched with water and extracted with ether (three times). The ether layer was washed with 1 N hydrochloric acid (three times), followed by saturated sodium chloride, and was dried over magnesium sulfate and concentrated. After flash chromatography (silica gel/15%–20% ethyl acetate:hexane), 5.45 g of the title A compound as an oil was obtained.

Calc'd for C$_{21}$H$_{20}$NF$_3$O$_3$.0.53 H$_2$O: C, 62.92; H, 5.29; N, 3.49; Found: C, 63.03; H, 5.25; N, 3.38.

Step 2: Preparation of (3R-cis)-1,3,4,5-tetrahydro-1-(formylmethyl)-3-hydroxy-4-(4-methoxyphenyl)-6-(trifluoromethyl)-2H-1-benzazepin-2-one The step 1 compound (5.32 g; 13.59 mmole) in methanol (140 ml) and methylene chloride (70 ml) was cooled to −78° C. and treated with O$_3$ with stirring. The blue mixture was allowed to stir for 10 minutes and then was flushed with oxygen. The solution was treated with DMS (2 ml) and the solvent was distilled off in the hood. The crude material was flashed (silica gel/2-0%–60% ethyl acetate:hexane), and the isolated material was co-evaporated with hexane (twice), leaving 4.50 g of the step 2 compound as a white solid, melting point 64°–68° C.

1.0 g (2.54 mmol) of (3R-cis)-1,3,4,5-Tetrahydro-1-(formylmethyl)-3-hydroxy-4-(4-methoxyphenyl)-6-(trifluoromethyl)-2H-1-benzazepin-2-one (described in steps 1 and 2) was placed in 25 ml of methanol solvent. 0.4 ml (1.1 eq.; 2.80 mmol) of 1-(2-Aminoethyl)-piperidine was added to the solution, followed by 0.125 g of 10% palladium on charcoal. The resulting suspension was stirred at room temperature under an atmosphere of hydrogen (balloon) for 18 hours. Thin layer chromatography at this point showed absence of the initial compound. The remaining reaction mixture was filtered and evaporated to 1.28 g of a viscous yellow oil, which was purified by flash chromatography to give 1.12 g (88%) of a white foam.

1.12 g (2.21 mmol) of the above white foam amine was placed in solution with 20 ml of ether. Saturated hydrogen chloride/ethyl ether was added to the solution to form its dihydrochloride salt. Precipitation from ether/chloroform gave 0.88 g (a 69% yield) of a white, amorphous solid.

Melting point: 226°–227° (dec); [α]$_D^{25}$ +79.4 (c 1.05%, methanol).

Analysis Calculated for $C_{27}H_{36}Cl_2F_3N_3O_3$: C,56.05; H,6.27; Cl,12.26; F,9.85, N,7.27. Found: C,56.20; H,6.50; Cl,12.22; F,9.97; N,7.19.

EXAMPLE 2

(3R-cis)-1,3,4,5-Tetrahydro-3-hydroxy-4-(4-methoxyphenyl)-1-[2-[[2-(4-morpholinyl)ethyl]amino]ethyl]-6-(trifluoromethyl)-2H-1-benzazepin-2-one, dihydrochloride.

1.0 g (2.54 mmol) of (3R-cis)-1,3,4,5-Tetrahydro-1-(formylmethyl)-3-hydroxy-4-(4-methoxyphenyl)-6-(trifluoromethyl)-2H-1-benzazepin-2-one (described in steps 1 and 2, Example 1) was placed in 25 ml of methanol. 0.37 ml (1.1 eq.; 2.80 mmol) of 4-(2-Aminoethyl)-morpholine was added to the solution, followed by 125 mg of 10% palladium on charcoal. The resulting suspension was stirred at room temperature under an atmosphere of hydrogen (balloon) for 18 hours. At that point, thin layer chromatography showed absence of the initial solute. Filtration through "Celite" TM and evaporation resulted in 1.0 g (78%) of a white foam.

The above secondary amine was combined with an additional 0.35 g (1.35 g overall; 2.65 mmol) from another experiment and dissolved in 25 ml of dry ether. A saturated solution of hydrogen chloride/diethyl ether was then added to form 1.0 g of the dihydrochloride salt, which could not be recrystallized. Therefore, the free base was regenerated and dissolved in 100 ml of ether. A solution of 0.25 g of oxalic acid in 10 ml of methanol was added to make the oxalate salt, which could be recrystallized from 10% aqeuous acetonitrile. Regeneration of the free base followed by dihydrochloride salt formation as above gave 557 mg (a 36% yield) of a white solid.

Melting point: 180°-182° (dec); $[\alpha]_D^{25}$ +76.2° (c 1.05%, methanol).

Analysis Calculated for $C_{26}H_{32}F_3N_3O_4 \cdot 1.85HCl$: C,54.31; H,5.93, Cl,11.41; F,9.91; N,7.31 Found: C,54.63; H,6.21; Cl,11.27; F,9.57; N,7.25.

EXAMPLE 3

(3R-cis)-1,3,4,5-Tetrahydro-3-hydroxy-4-(4-methoxyphenyl)-1-[2-[[2-(2-pyridinyl)ethyl]amino]ethyl]-6-(trifluoromethyl)-2H-1-benzazepin-2-one, dihydrochloride.

Step 1: Formation of Oxalate Salt

Formation of this compound began with the following solution:

(1) 1.0 g (2.5 mmol) of a first solute, (3R-cis)-1,3,4,5-tetrahydro-1-(formylmethyl)-3-hydroxy-4-(4-methoxyphenyl)-6-(trifluoromethyl)-2H-1-benzazepin-2-one (described in steps 1 and 2, Example 1)

(2) 0.38 ml (3.0 mmol) of a second solute, 2-(2-aminoethyl)pyridine; and (3) 10 ml of methanol solvent.

This solution was stirred, treated with a cold slurry of 0.2 g of a catalyst (10% palladium on charcoal) in 5 ml of methanol, fitted with a 4 l hydrogen balloon, and stirred for 20 hours at room temperature.

Thin layer chromatography at that point showed presence of only a weak trace of the first solute. Therefore, we filtered off the catalyst under argon and washed the solution with methanol. The combined filtrates then evaporated, leaving an oily residue. The residual oil was placed in 70 ml of ethyl acetate, washed with water (3×5 ml) and brine (5 ml), dried with magnesium sulfate, and filtered.

The resulting filtrate was treated with a solution of 0.23 g (2.5 mmol) of oxalic acid in 10 ml of ether to form an oxalate salt.

The oxalate salt separated as a gelatinous solid, which became somewhat more granular on standing; after cooling overnight, a colorless solid remained. This solid was filtered, washed with ether, and dried, leaving 1.22 g of a salt with a melting point of 176°-178°.

Analysis Calculated for $C_{27}H_{28}F_3N_2O_3 \cdot C_2H_2O_4 \cdot 0.5H_2O$: C,58.19; H,5.22; N,7.02; F,9.52 Found: C,58.00; H,5.15; N,7.21; F,9.19

Step 2: Formation of the Hydrochloride Salt

The oxalate salt was converted to a base by treatment with a solution of 0.5 g of potassium carbonate in 20 ml of water and ethyl acetate extractions. The resulting ethyl acetate solution was dried and treated with 1 ml of 5N ethanolic hydrochloric acid. Some methanol was added to redissolve precipitated material, and the water and methanol solvents were removed on a rotary evaporator. The remaining residue was rubbed under ether, the evaporation was repeated, and the resulting residue was pump-dried. In result, 1.15 g of solid remained, having a melting point of 59°-63° C.

Thereafter, 15 ml of warm acetonitrile was added to the solid. The solid therefore crystallized, leaving a colorless material weighing 0.92 g (a 64% yield) having a melting point of 195°-197°; $[\alpha]_D^{25}$ +59.0° (c 1%, methanol).

Analysis Calculated for $C_{27}H_{28}F_3N_3O_3 \cdot 2HCl \cdot 0.5H_2O$: C,55.77; H,5.37; N,7.23; Cl,12.20 Found: C,55.61; H,5.44; N,7.25; Cl,12.27

EXAMPLE 4

(3R-cis)-1,3,4,5-Tetrahydro-3-hydroxy-4-(4-methoxyphenyl)-1-[2-[[2-(4-pyridinyl)ethyl]amino]ethyl]-6-(trifluoromethyl)2H-1-benzazepin-2-one, dihydrochloride.

Step 1: Formation of Oxalate Salt

Formation of this compound began with the following solution:

(1) 2.5 mmol of a first solute, (3R-cis)-1, 3,4,5-tetrahydro-1-(formylmethyl)-3-hydroxy-4-(4-methoxyphenyl)-6-(trifluoromethyl)-2H-1-benzazepin-2-one (described in steps 1 and 2, Example 1);

(2) 0.37 g (3.0 mmol) of a second solute, 4-(2-aminoethyl)pyridine; and (3) 10 ml of methanol solvent.

This solution was stirred, treated with a cold slurry of 0.2 g of a catalyst (10% palladium on charcoal) in 5 ml of methanol, fitted with a 5 l hydrogen balloon, and stirred for 20 hours at room temperature.

At that time, thin layer chromatography showed only a weak trace of the first solute present. The solution was then treated first as in Example 3 (step 1, second paragraph) and second with 0.23 g oxalic acid in ether. These procedures yielded 1.25 g of an oxalate salt having a melting point of 78°-81°.

Analysis Calculated for $C_{27}H_{28}F_3N_3O_3 \cdot C_2H_2O_4 \cdot 1.5H_2O$: C,56.49; H,5.39; N,6.82 Found: C,56.61; H,5.36; N,6.97

The oxalate salt was converted to a base by treatment with potassium carbonate and ethyl acetate extractions. This treatment yielded 1.13 g of solid hydrochloride salt having a melting point of 82°-85°.

The above salt was stirred with 70 ml of hot acetonitrile, forming an insoluble yellow oil. The material that separated as an oil gradually solidified on standing at room temperature with occasional rubbing. A colorless solid resulted that, after cold storage, weighed 0.76 g (a 53% yield) with a melting point of 153°–155°; $[\alpha]_D^{25°} + 67°$ (c 1% methanol).

Analysis Calculated for $C_{27}H_{28}F_3N_2O_3.2$ HCl. $H_2O$: C,54.92; H,5.46; N,7.12; Cl,12.01 Found: C,55.01; H,5.83; N,6.94; Cl,12.41

EXAMPLE 5

(3R-cis)-1,3,4,5-Tetrahydro-3-hydroxy-1-[2-[[3-(1H-imidazol-1-yl)propyl]amino]ethyl]-4-(4-methoxyphenyl)-6-(trifluoromethyl)-2H-1-benzazepin-2-one, fumarate (1:2) salt.

Formation of this compound began with a solution of:
(1) 1 g (2.54 mmol) of a first solute, (3R-cis)-1,3,4,5-tetrahydro-1-(formylmethyl)-3-hydroxy-4-(4-methoxyphenyl)-6-(trifluoromethyl)-2H-1-benzazepin-2-one (described in steps 1 and 2, Example 1);
(2) 0.4 ml (3.30 mmol) of a second solute, 1-(3-aminopropyl)imidazole;
(3) a catalyst, 10% palladium on charcoal; and
(4) 25 ml of methanol as a solvent.

This mixture was hydrogenated at room temperature for 20 hours using a balloon apparatus. The catalyst was removed by filtration through "Celite" TM, and the filtrate was concentrated to afford 1.4 g of a crude yellow oil.

This yellow oil residue was loaded onto a 5×25 cm silicon dioxide column and eluted with a mixture of dichloromethane:methanol:triethylamine 95.5:4:0.5. The pure fractions were concentrated to afford 1.105 g (87%) of free amine as a colorless oil.

987 mg (1.96 mmol) of this free amine base was dissolved in 5 ml of methanol. Exactly 2 eq of fumaric acid (455 mg; 3.92 mmol) was added to the solution in a minimal amount of hot methanol. The resulting solution was concentrated to dryness, triturated with diethyl ether and vacuum-dried. A white solid weighing 1.292 mg (a 90% yield) resulted.

Melting point: 142°–150°; $[\alpha]_D^{25°} + 61.6°$ (c 1.05%, methanol).

Analysis Calculated for $C_{26}H_{29}F_3N_4O_3.2C_4H_4O_4.1.75$ $H_2O$ C,53.29; H,5.33; F,7.44; N,7.31 Found: C,53.37; H,5.15; F,7.36; N,7.12

EXAMPLE 6

(3R-cis)-1,3,4,5-Tetrahydro-3-hydroxy-4-(4-methoxyphenyl)-1-[2-[[2-(1-methyl-1H-pyrrol-2-yl)ethyl]amino]ethyl]-6-(trifluoromethyl)-2H-1-benzazepin-2-one, fumarate (1:1) salt.

Formation of this compound began with a solution of:
(1) 1 g (2.54 mmol) of a first solute, (3R-cis)-1,3,4,5-tetrahydro-1-(formylmethyl)-3-hydroxy-4-(4-methoxyphenyl)-6-(trifluoromethyl)-2H-1-benzazepin-2-one (described in steps 1 and 2, Example 1);
(2) 0.427 ml (3.30 mmol) of a second solute, 2-(2-aminoethyl)-1-methylpyrrole;
(3) a catalyst, 10% palladium on charcoal; and
(4) 25 ml of methanol as a solvent.

This solution was hydrogenated at room temperature for 20 hours, using a balloon apparatus. The catalyst was removed by filtration through "Celite" TM, and the filtrate was concentrated.

The filtration residue was loaded onto a 5×25 cm silicon dioxide column, which was eluted with 2% methanol/dichloromethane. This procedure afforded only marginal purification, so the crude product was rechromatographed on a 5×25 cm silicon dioxide column, which was eluted with 1% methanol/dichloromethane. Pure fractions were concentrated to afford 790 mg (a 61% yield) of the free amine.

720 mg (1.4 mmol) of the free amine was dissolved in approximately 5 ml of methanol. 2 eq of fumaric acid, dissolved in a minimum amount of hot methanol, were then added. This mixture was concentrated to an off-white solid residue. This residue was recrystallized from hot isopropanol and vacuum dried at 50° C. to afford 520 mg (a 60% yield) of Example 6 as an off-white, mono-fumarate.

Melting point: 187°–189° C. (dec); $[\alpha]_D^{25°} + 55.7°$ (c 0.94%, HOAc).

Analysis Calculated for $C_{27}H_{30}F_3N_3O_3.C_4H_4O_4.0.26$ $H_2O$: C,59.84; H,5.59; F,9.16; N,6.75 Found: C,59.88; H,5.62; F,9.06; N,6.71

EXAMPLE 7

(3R-cis)-1-[2-[[2-(2-Furanyl)ethyl]amino]ethyl]-1,3,4,5-tetrahydro-3-hydroxy-4-(4-methoxyphenyl)-6-(trifluoromethyl)-2H-1-benzazepin-2-one, fumarate (1:1) salt.

Step 1: Preparation of the First Intermediate, 2-(2-nitroethenyl)furan 21.5 ml (3N) of potassium hydroxide was cooled to 0° C. 3.6 ml (65.2 mmol) of nitromethane was added to produce a pale yellow solution. Approximately 10 g of ice was then added, followed by freshly distilled furfural (5.7 g; 59.3 mmol). The reaction became turbid for a short time and then clarified to a yellow solution.

The reaction mixture was neutralized with 1N hydrochloric acid and extracted with diethyl ether. The diethyl ether layer was washed with brine, dried with magnesium sulfate, and concentrated to afford an orange oil.

This oil was chromatographed on a 5×25 cm silicon dioxide column using hexane:ethyl acetate, 5:1, as eluant. The pure, less polar fractions were concentrated to afford 300 mg (a 4% yield) of the first intermediate a yellow solid. The pure, more polar fractions were concentrated to afford 5.08 g (a 55% yield) of 2-(1-hydroxy-2-nitro)ethyl furan.

5 g (31.8 mmol) of the latter compound was heated to 100° C. in 200 ml of toluene in the presence of 575 mg of p-toluene sulfonic acid, monohydrate, for 15 minutes. A black gum formed, but thin layer chromatography of the supernatant indicated formation of the first intermediate.

After cooling, the supernatant was washed with water, dried with magnesium sulfate, and concentrated to a brown residue. This residue was filtered through a plug of silicon dioxide in a 600 ml scintered glass funnel using a mixture of Hex:ethyl acetate, 5:1. The filtrate was concentrated to afford 530 mg (a 12% yield) of the desired compound as a yellow solid.

Step 2: Preparation of the Second Intermediate, 2-(2-aminoethyl)furan 800 mg (20 mmol) of lithium aluminum hydride was suspended in 30 ml of ethyl ether from a freshly opened can. 875 mg (6.3 mmol) of the first intermediate (see above) was placed in solution with 20 ml of ethyl ether. This solution was added dropwise to the hydride suspension for over 30 minutes, and the reaction mixture was stirred for an additional 90 minutes. At that time, the reaction was quenched by careful addition of 0.8 ml of water, followed by 0.8 ml of 15% sodium hydroxide, followed by 2.4 ml of water.

Sodium sulfate was then added, and the suspension was stirred for another 30 minutes. This solution was filtered through "Celite" TM, and the filter cake was thoroughly washed with ethyl ether. In result, the filtrate was concentrated to 800 mg of an orange oil. The oil was purified by Kiglerohr distillation at 90° C. and 30 mm Hg to afford a 425 mg (60%) yield of the second intermediate as a colorless liquid.

Step 3: Preparation of Example 7

Step 3 began with a solution of:
(1) 1 g (2.54 mmol) of a first solute, (3R-cis)-1,3,4,5-tetrahydro-1-(formylmethyl)-3-hydroxy-4-(4-methoxyphenyl)-6-(trifluoromethyl)-2H-1-benzazepin-2-one (described in steps 1 and 2, Example 1);
(2) 400 mg (3.6 mmol) of the second intermediate as a second solute;
(3) a catalyst, 10% palladium on charcoal; and
(4) 25 ml of methanol as a solvent.

This solution was hydrogenated by balloon at room temperature for 20 hours. The catalyst was removed by filtration through "Celite" TM, and the filtrate was concentrated to afford 1.25 g of a crude residue.

This residue was loaded onto a 5×30 cm silicon dioxide column, which was eluted with a mixture of 3 l of 1% methanol/dichloromethane and 1 l of 2% methanol/dichloromethane. Pure fractions were combined and concentrated to afford 676 mg of the free base. Mixed fractions were purified by preparative thin layer chromatography. Extraction afforded an additional 78 mg, which gave a total of 754 mg (a 61% yield) of free base.

676 mg (1.38 mmol) of the free base was dissolved in 5 ml of methanol and exactly 1 eq of fumaric acid was added as a solution in a minimum amount of hot methanol. The resulting solution was concentrated and triturated with ethyl ether to afford 704 mg (an 84% yield) of a white solid.

Melting point: 175°–177° C.; $[\alpha]_D^{25°} +87.3°$ (c 1.05%, 95% ethanol).

EXAMPLE 8

(3R-cis)-1,3,4,5-Tetrahydro-3-hydroxy-4-(4-methoxyphenyl)-1-[2-[[2-(1-methyl-1H-indol-3-yl)ethyl]amino]ethyl]-6-(trifluoromethyl)-2H-1-benzazepin-2-one, sesquihydrochloride.

Step 1: Preparation of the First Intermediate, 1-methyl tryptamine

This step began with a solution of:
(1) 1.6 g (10 mmol) of tryptamine; and
(2) 20 ml of dimethylformamide.
This solution was added dropwise to a suspension of:
(1) 440 mg (11 mmol) of sodium hydride oil in
(2) 30 ml of dimethylformamide.
A dark brown solution resulted.

The dark brown solution was then stirred for 30 minutes at room temperature, cooled to 0° C., and mixed with methyl iodide. (The methyl iodide was purified before use by passing it through a column of basic alumina.) After stirring for an hour at room temperature, the reaction mixture was partitioned between ethyl acetate and water. The ethyl acetate layer was washed with saturated brine and then dried by sodium sulfate filtration. The filtrate was concentrated, the filtration residue loaded onto a 5×25 cm silicon dioxide column, and the column eluted with dichloromethane:methanol:triethylamine, 95:4:1. Pure fractions were concentrated to afford 970 mg (a 56% yield) of the first intermediate as a yellow oil.

Step 2: Preparation of Example 8

This step began with a mixture of:
(1) 1 g (2.54 mmol) of a first solute, (3R-cis)-1,3,4,5-Tetrahydro-1-(formylmethyl)-3-hydroxy-4-(4-methoxyphenyl)-6-(trifluoromethyl)-2H-1-benzazepin-2-one (described in steps 1 and 2, Example 1);
(2) 575 mg (3.30 mmol) of 1-methyl tryptamine as a second solute;
(3) 150 mg of a catalyst, 10% palladium on charcoal; and
(4) 25 ml of methanol as a solvent.

This mixture was hydrogenated by balloon at room temperature for 20 hours. The catalyst was removed by filtration through "Celite" TM, and the filtrate was concentrated. The filtration residue was loaded onto a 5×20 cm silicon dioxide column, which was eluted with 3% methanol/dichloromethane. Pure fractions were concentrated to afford 1.17 g (an 84% yield) of free amine as a light yellow oil.

Saturated hydrochloride/ethyl ether was added to a solution of 950 mg (1.72 mmol) of the free amine in approximately 4 ml of dry ethyl ether. The hydrochloride salt of the free amine was thereby formed. The salt was filtered and recrystallized from chloroform/ethyl ether to afford 750 mg (a 64% yield) of Example 8 as a white solid.

Melting point: 134°–140° C.; $[\alpha]_D^{25°} +74.0°$ (c 1.05%, methanol).

Analysis Calculated for $C_{31}H_{32}F_3N_3O_3 \cdot 1.6$ HCl: C,61.04; H,5.55; Cl,9.30; F,9.34; N,6.89 Found: C,61.27; H,5.52; Cl,9.30; F,9.35; N,6.73.

While this invention has been described by reference to specific examples, these examples are meant to be illustrative rather than limiting. The inventors and their assignees intend to be limited only by the scope of the claims appended hereto.

What is claimed is:

1. A compound having the formula

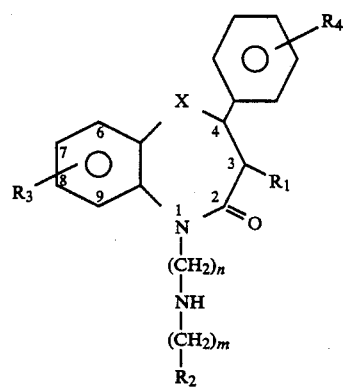

or a pharmaceutically acceptable salt thereof, wherein:
X is —CH$_2$— or —S—;
R$_1$ is

or —O—Y$_3$;

R$_2$ is imidazolyl, furanyl, pyridinyl, pyrrolyl, indolyl, piperidinyl, morpholinyl, or any of such groups substituted with alkyl;

R$_3$ and R$_4$ are each independently hydrogen, halogen, alkyl, alkoxy, aryloxy, arylalkoxy, arylalkyl, cyano, hydroxy, alkanoyloxy,

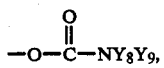

fluoro-substituted alkoxy, fluoro-substituted alkyl, (cycloalkyl)alkoxy, —NO$_2$, —NY$_{10}$Y$_{11}$, —S(O)$_k$alkyl, —S(O)$_k$aryl,

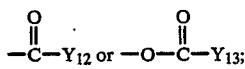

n is 0, 1, 2 or 3;
m is 0, 1, 2 or 3;
k is 0, 1 or 2;
Y$_1$ and Y$_2$ are each independently hydrogen or alkyl; or Y$_1$ is hydrogen and Y$_2$ is alkenyl, alkynyl, aryl, or cycloalkyl; or Y$_1$ and Y$_2$, together with the carbon atom to which they are attached, are cycloalkyl;
Y$_3$ is hydrogen, alkyl, alkanoyl, alkenyl, arylcarbonyl, or

Y$_8$ and Y$_9$ are each independently hydrogen, alkyl, or aryl; or Y$_8$ and Y$_9$, together with the nitrogen atom to which they are attached, are pyrrolidinyl, piperidinyl, or morpholinyl;
Y$_{10}$ and Y$_{11}$ are each independently hydrogen, alkyl, alkanoyl, arylcarbonyl, or

Y$_{12}$ is hydroxy, alkoxy, aryloxy, amino, alkylamino, or dialkylamino; and
Y$_{13}$ is alkyl, alkoxy or aryloxy; and wherein:
"alkyl" and "alkoxy" refer to straight and branched chain hydrocarbon groups having 1 to 10 carbon atoms;
"alkenyl" and "alkynyl" refer to straight and branched chain hydrocarbon groups having 2 to 10 carbon atoms;
"aryl" refers to unsubstituted phenyl groups and to phenyl groups substituted with 1, 2, or 3 groups selected from amino, alkylamino, dialkylamino, nitro, halogen, hydroxyl, trifluoromethyl, alkyl (of 1 to 4 carbon atoms), alkoxy (of 1 to 4 carbon atoms), alkylthio (of 1 to 4 carbon atoms), alkanoyloxy, carbamoyl, and carboxyl;

"alkanoyl" refers to groups of the formula alkyl

having 2 to 11 carbon atoms;
"cycloalkyl" refers to cyclic hydrocarbon groups having 3, 4, 5, 6, or 7 carbon atoms; and
"fluoro-substituted alkyl" and "fluoro-substituted alkoxy" refer to alkyl and alkoxy groups in which one or more hydrocarbon atoms are replaced by fluorine atoms.

2. A compound in accordance with claim 1 wherein R$_1$ is

3. A compound in accordance with claim 1 wherein R$_1$ is —O—Y$_3$.

4. A compound in accordance with claim 1, wherein R$_1$ is hydroxyl.

5. A compound in accordance with claim 1, wherein R$_2$ is imidazolyl, furanyl, pyridinyl, methylpyrrolyl, methylindolyl, piperidinyl, or morpholinyl.

6. A compound in accordance with claim 1, wherein R$_3$ is trifluoromethyl or halogen.

7. A compound in accordance with claim 1, wherein R$_4$ is located in the 4-position of the phenyl ring to which it is attached, and is hydroxy, alkoxy, alkylamino, aryloxy, or arylalkoxy.

8. A compound in accordance with claim 1 wherein R$_4$ is 4-methoxy.

9. The compound in accordance with claim 1, (3R-cis)-1,3,4,5-tetrahydro-3-hydroxy-1-[2-[[3-(1H-imidazol-1-yl)propyl]amino]ethyl]-4-(4-methoxyphenyl)-6-(trifluoromethyl)-2H-1-benzazepin-2-one, fumarate (1:2)salt.

10. The compound in accordance with claim 1, (3R-cis)-1,3,4,5-tetrahydro-3-hydroxy-4-(4-methoxyphenyl)-1-[2-[[2-(4-pyridinyl)ethyl]amino]ethyl]-6-(trifluoromethyl)-2H-1-benzazepin-2-one, dihydrochloride.

11. The compound in accordance with claim 1, (3R-cis)-1,3,4,5-tetrahydro-3-hydroxy-4-(4-methoxyphenyl)-1-[2-[[2-(1-methyl-1H-indol-3-yl)ethyl]amino]ethyl]-6-(trifluoromethyl)-2H-1-benzazepin-2-one, sesquihydrochloride.

12. The compound in accordance with claim 1, (3R-cis)-1-[2-[[2-(2-furanyl)ethyl]amino]ethyl]-1,3,4,5-tetrahydro-3-hydroxy-4-(4-methoxyphenyl)-6-(trifluoromethyl)-2H-1-benzazepin-2-one, fumarate (1:1) salt.

13. The compound in accordance with claim 1, (3R-cis)-1,3,4,5-tetrahydro-3-hydroxy-4-(4-methoxyphenyl)-1-[2-[[2-(1-methyl-1H-pyrrol-2-yl)ethyl]amino]ethyl]-6-(trifluoromethyl)-2H-1-benzazepin-2-one, fumarate (1:1) salt.

14. The compound in accordance with claim 1, (3R-cis)-1,3,4,5-tetrahydro-3-hydroxy-4-(4-methoxyphenyl)-1-[2-[[2-(1-piperidinyl)ethyl]amino]ethyl]-6-(trifluoromethyl)-2H-1-benzazepin-2-one, dihydrochloride.

15. The compound in accordance with claim 1, (3R-cis)-1,3,4,5-tetrahydro-3-hydroxy-4-(4-methoxyphenyl)-1-[2-[[2-(4-morpholinyl)ethyl]amino]ethyl]-6-(trifluoromethyl)-2H-1-benzazepin-2-one, dihydrochloride.

16. The compound in accordance with claim 1, (3R-cis)-1,3,4,5-tetrahydro-3-hydroxy-4-(4-methoxyphenyl)-1-[2-[[2-(2-pyridinyl)ethyl]amino]ethyl]-6-(trifluoromethyl)-2H-1-benzazepin-2-one, dihydrochloride.

17. A method of treating a host having a disease susceptible to treatment with a vasodilator, which comprises administering to said host an effective amount of a compound as defined in claim 1.

18. A compound having the formula

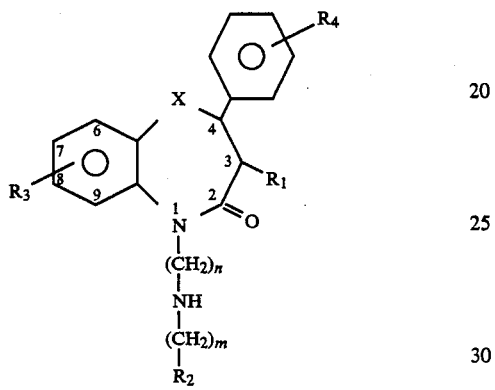

or a pharmaceutically acceptable salt thereof, wherein:
X is —CH$_2$— or —S—;
R$_1$ is

or —O—Y$_3$;
when X is —CH$_2$—, R$_2$ is imidazolyl, furanyl, pyridinyl, pyrrolyl, indolyl, piperidinyl, morpholinyl, or any of such groups substituted with alkyl; when X is —S—, R$_2$ is morpholinyl, piperidinyl, or any of such groups substituted with alkyl;

R$_3$ and R$_4$ are each independently hydrogen, halogen, alkyl, alkoxy, aryloxy, arylalkoxy, arylalkyl, cyano, hydroxy, alkanoyloxy,

fluoro-substituted alkoxy, fluoro-substituted alkyl, (cycloalkyl)alkoxy, —NO$_2$, —NY$_{10}$Y$_{11}$, —S(O)$_k$alkyl, —S(O)$_k$aryl,

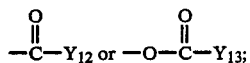

n is 0, 1, 2 or 3;
m is 0, 1, 2 or 3;
k is 0, 1 or 2;
Y$_1$ and Y$_2$ are each independently hydrogen or alkyl; or Y$_1$ is hydrogen and Y$_2$ is alkenyl, alkynyl, aryl, or cycloalkyl; or Y$_1$ and Y$_2$, together with the carbon atom to which they are attached, are cycloalkyl;
Y$_3$ is hydrogen, alkyl, alkanoyl, alkenyl, arylcarbonyl, or

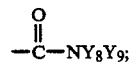

Y$_8$ and Y$_9$ are each independently hydrogen, alkyl, or aryl; or Y$_8$ and Y$_9$, together with the nitrogen atom to which they are attached, are pyrrolidinyl, piperidinyl, or morpholinyl;
Y$_{10}$ and Y$_{11}$ are each independently hydrogen, alkyl, alkanoyl, arylcarbonyl, or

Y$_{12}$ is hydroxy, alkoxy, aryloxy, amino, alkylamino, or dialkylamino; and
Y$_{13}$ is alkyl, alkoxy or aryloxy; and wherein:
"alkyl" and "alkoxy" refer to straight and branched chain hydrocarbon groups having 1 to 10 carbon atoms;
"alkenyl" and "alkynyl" refer to straight and branched chain hydrocarbon groups having 2 to 10 carbon atoms;
"aryl" refers to unsubstituted phenyl groups and to phenyl groups substituted with 1, 2, or 3 groups selected from amino, alkylamino, dialkylamino, nitro, halogen, hydroxyl, trifluoromethyl, alkyl (of 1 to 4 carbon atoms), alkoxy (of 1 to 4 carbon atoms), alkylthio (of 1 to 4 carbon atoms), alkanoyloxy, carbamoyl, and carboxyl;
"alkanoyl" refers to groups of the formula alkyl

having 2 to 11 carbon atoms;
"cycloalkyl" refers to cyclic hydrocarbon groups having 3, 4, 5, 6, or 7 carbon atoms; and
"fluoro-substituted alkyl" and "fluoro-substituted alkoxy" refer to alkyl and alkoxy groups in which one or more hydrocarbon atoms are replaced by fluorine atoms.

* * * * *